(12) United States Patent
Pfichner et al.

(10) Patent No.: US 7,472,701 B2
(45) Date of Patent: Jan. 6, 2009

(54) AEROSOL GENERATION DEVICE AND INHALATION DEVICE THEREWITH

(75) Inventors: Andreas Pfichner, Unterhaching (DE); Gerhard Pumm, Oberau (DE)

(73) Assignee: PARI Pharma GmbH, Starnberg (DE)

( * ) Notice: Subject to any disclaimer, the term of this patent is extended or adjusted under 35 U.S.C. 154(b) by 0 days.

(21) Appl. No.: 11/094,561

(22) Filed: Mar. 30, 2005

(65) Prior Publication Data
US 2005/0224076 A1 Oct. 13, 2005

(30) Foreign Application Priority Data
Apr. 7, 2004 (DE) .................. 10 2004 016 985

(51) Int. Cl.
*A61M 15/00* (2006.01)
*A61M 16/10* (2006.01)

(52) U.S. Cl. .................. 128/203.12; 128/200.14; 128/203.19; 128/205.24; 128/200.13; 128/200.11; 128/200.21; 128/200.22; 128/201.28

(58) Field of Classification Search ............ 128/200.14, 128/203.19, 205.24, 200.13, 200.11, 200.21, 128/200.22, 201.28
See application file for complete search history.

(56) References Cited

U.S. PATENT DOCUMENTS

| | | | | |
|---|---|---|---|---|
| 3,387,607 A | * | 6/1968 | Gauthier et al. | 128/200.16 |
| 4,533,082 A | * | 8/1985 | Maehara et al. | 239/102.2 |
| 4,702,418 A | * | 10/1987 | Carter et al. | 239/101 |
| 6,526,976 B1 | * | 3/2003 | Baran | 128/207.14 |
| 6,629,646 B1 | * | 10/2003 | Ivri | 239/4 |
| 2003/0150928 A1 | | 8/2003 | Watanabe et al. | |
| 2004/0089295 A1 | | 5/2004 | Gallem et al. | |

FOREIGN PATENT DOCUMENTS

| | | |
|---|---|---|
| DE | 102 29 889 A1 | 1/2004 |
| EP | 0 084 458 A2 | 7/1983 |
| EP | 0 615 470 B1 | 9/1994 |
| WO | WO 02/064265 A2 | 8/2002 |
| WO | WO 2004/004813 A1 | 1/2004 |

OTHER PUBLICATIONS

Maehara et al., "Influence of the vibrating system of a multipinhole-plate ultrasonic nebulizer on its performance", Rev.Sci.Instrum. 57 (11), Nov. 1986, pp. 2870-2876.

* cited by examiner

*Primary Examiner*—Patricia M Bianco
*Assistant Examiner*—Nihir Patel
(74) *Attorney, Agent, or Firm*—Wolf, Greenfield & Sacks, P.C.

(57) ABSTRACT

An aerosol generation device comprising an oscillatable membrane (1) for the nebulization of a liquid, having a first curved region (11), and an oscillation generating device (2, 3) by which the membrane can be caused to oscillate such that a liquid disposed on one side of the membrane is nebulized through the oscillating membrane and is present on the other side of the membrane as an aerosol. The membrane has at least a second region (12) which is surrounded by the first region (11). The first region (11) and the second region (12) have different curvatures ($1/r_1$, $1/r_2$).

15 Claims, 5 Drawing Sheets

AEROSOL GENERATION DEVICE AND INHALATION DEVICE THEREWITH

Figure 1:
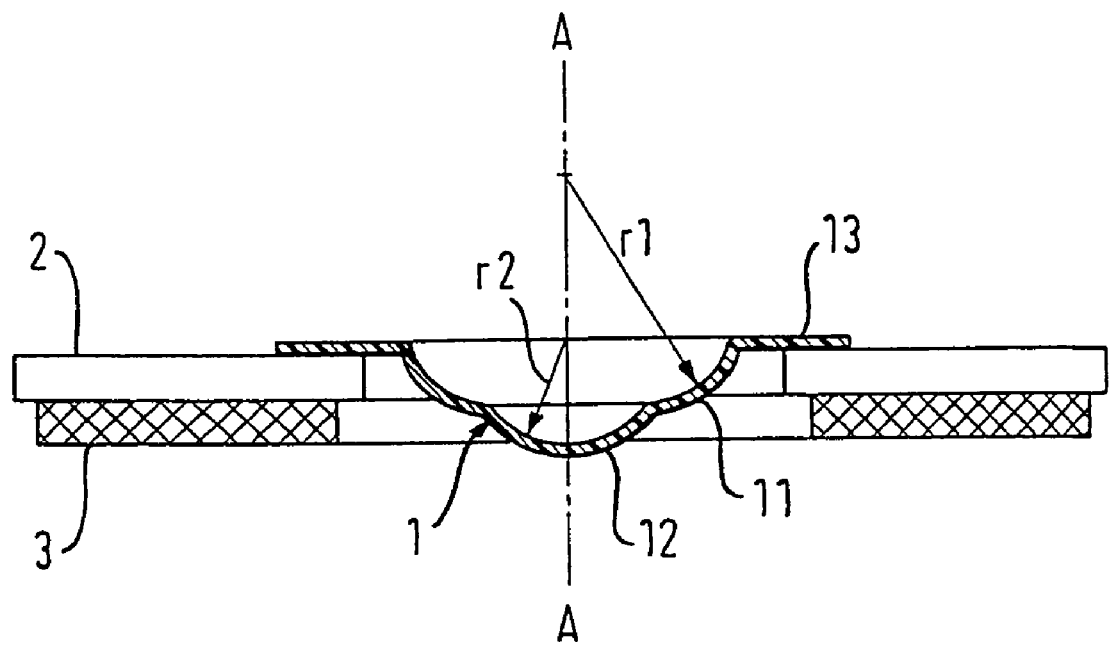

The invention relates to an aerosol generation device comprising an oscillatable membrane and an oscillation generating device, as well as an inhalation therapy device comprising such an aerosol generation device.

Aerosol generation devices are in particular known in the prior art, but not only for inhalation therapy devices, in which an oscillatable membrane is caused to oscillate by an oscillation generation device, and in which a liquid, which is applied to the one side of the membrane, passes through the oscillating membrane and is output on the other side of the membrane as an aerosol. It is known, e.g. from EP 0 084 458 A, to provide the oscillatable membrane with a curved region and to arrange holes in the membrane at locations where the oscillation pattern of the membrane has antinodes. It is known from EP 0 615 470 A that the oscillatable membrane can be caused to perform bending oscillations by the oscillation generating device.

In the known embodiments of the above-mentioned aerosol generation device, it is disadvantageous in particular for an application in inhalation therapy devices that greater amounts of liquid often adhere to the side of the membrane facing the aerosol which unify to droplets and close several of the holes in the membrane. The transport of liquid and the generation of a sufficient amount of aerosol in a desired region of droplet spectrum range is thereby impaired. Some of the droplets may also separate from the oscillating membrane which may have an adverse effect on the aerosol droplet spectrum. It is therefore required to prevent by additional measures that too great an amount of liquid can accumulate at the aerosol side of the membrane and that too large droplets separate.

To this end, it has proven to be expedient that the fluid used for the generation of droplets is stored in a reservoir under negative pressure, as is the case with a device described e.g. in WO 02/064265. This device has a lid for closing the fluid reservoir which builds up a negative pressure in the reservoir when being closed. Due to the negative pressure, the fluid does not accidentally escape from the perforated membrane. An unintentional and undesired droplet formation on the membrane can be prevented thereby which would impair an aerosol generation and lead to loss of fluid. However, this device is very complex and does not only require a fluid-tight, but also a gas-tight reservoir for maintaining the negative pressure. In addition, the proper operation of the device depends on a correct operation of the lid.

On this background, it is the object of the invention to provide an aerosol generation device which avoids the indicated problems, which is particularly suited for inhalation therapy devices and in which, without providing additional measures, the risk of adherence of liquid to the membrane on the side facing the aerosol is reduced.

This object is achieved by an aerosol generation device comprising an oscillatable membrane for nebulizing a liquid having a first curved region, and an oscillation generating device by which the membrane can be caused to oscillate such that a liquid disposed on one side of the membrane is nebulized through the oscillating membrane and is present on the other side of the membrane as an aerosol, wherein the membrane has at least a second region which is surrounded by the first region, and wherein the first region and the second region have different curvatures. Therein, the curvature of the second region can be advantageously also Zero, so that the second region is plane.

A transition edge is formed at the transition between the first region and the second region which defines an oscillation node line and, therefore, an oscillation can be generated in which an oscillation node line is present at the transition edge, when the oscillation generating device is driven in a suitable manner and the oscillatable membrane is thereby excited. The oscillation of the membrane is thereby influenced such that less liquid adheres to the aerosol side of the membrane.

The effect can be further enhanced when holes are only present in the first region and second region of the membrane through which the liquid can pass. A further enhancement is possible when the hole density in areas of a high oscillation amplitude is increased, for example, in that the holes have a greater density at a center line of the first region, or in that the holes have a greater density in the center of the second region. According to a preferred embodiment, the second region only has holes which are arranged in the center of the region. In connection therewith it is possible that the holes of zones having a higher hole density pass into zones having a lower hole density until there are no longer holes in a zone in the vicinity of the transition edge. However, the distribution of the holes can also abruptly pass from a zone having a constant hole density to a zone without holes extending until the transition edge. Based on a lower contribution to a nebulization by regions having a lower oscillation amplitude, the regions having a sufficiently high oscillation amplitude are advantageously only provided with holes, while regions having a low oscillation amplitude are not provided with holes. This allows that it is advantageously prevented that fluid passes through the holes in the membrane without being nebulized in regions which do not contribute to nebulization or which only have a low contribution to nebulization.

In order to be able to fasten the membrane according to the invention to the oscillation generation device, around the first region a third region is arranged, the curvature of which is Zero, i.e. which is plane.

By preventing that liquid adheres to the aerosol side of the membrane, the aerosol generation device according to the invention can be advantageously used in an inhalation therapy device comprising a liquid storing means for storing a liquid to be nebulized, wherein the supply of the liquid can be performed from the liquid storing means to the membrane through the membrane according to the invention at environmental pressure. Additional measures for preventing that liquid droplets adhere, such as e.g. the generation of a negative pressure in the liquid storing means, are not necessary.

Figure 2:
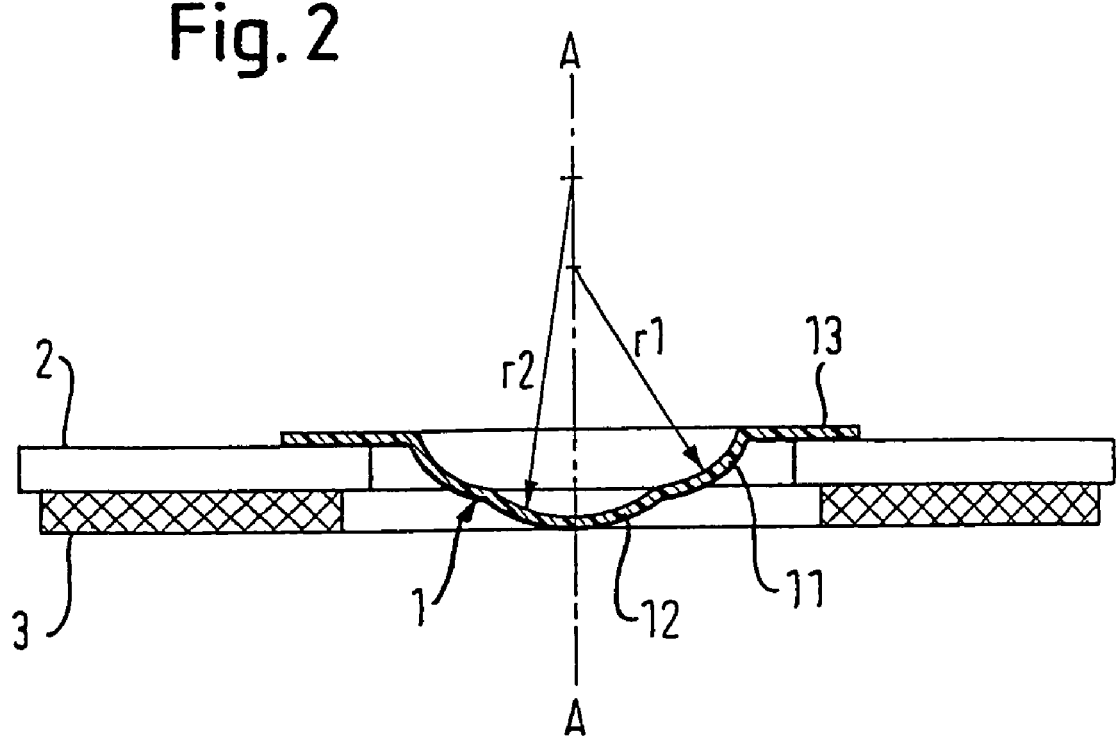
Figure 3:
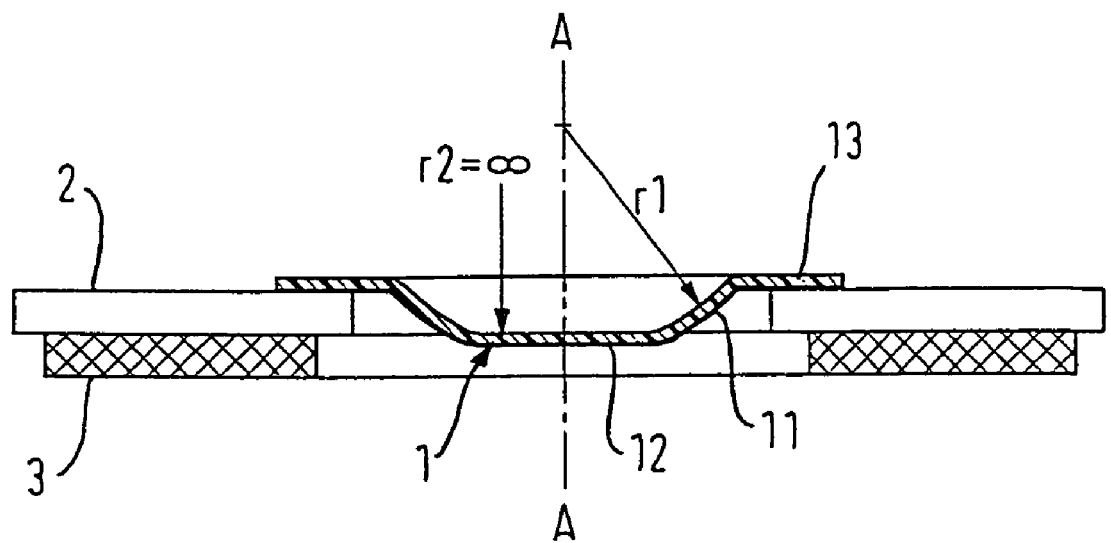
Figure 4:
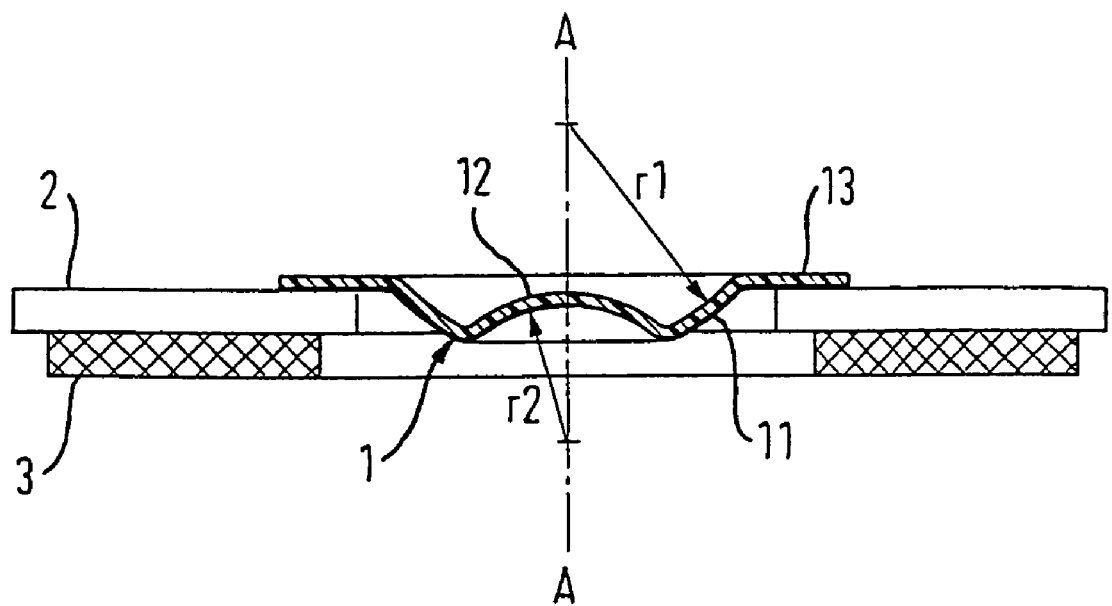
Figure 5:
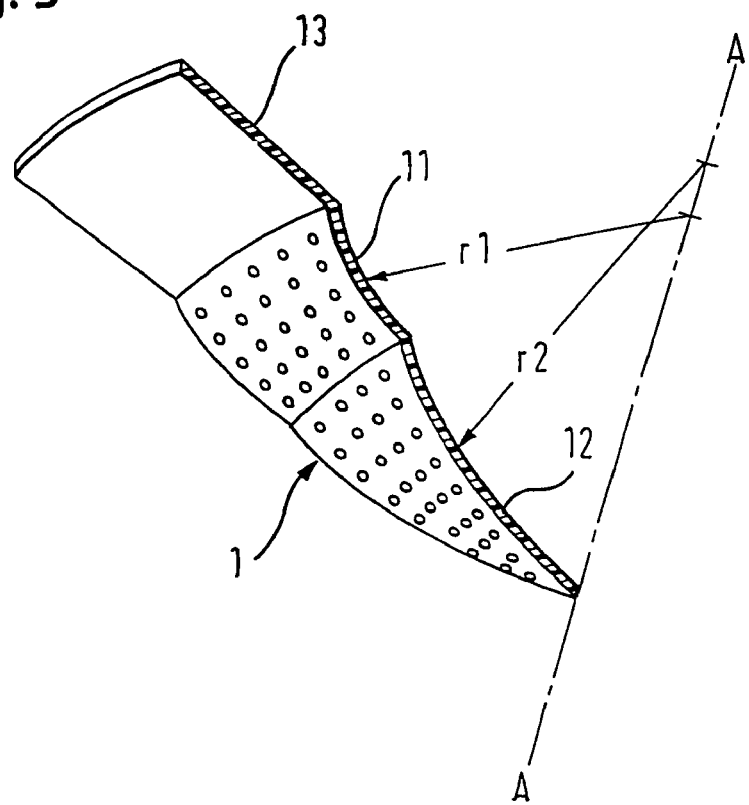
Figure 6:
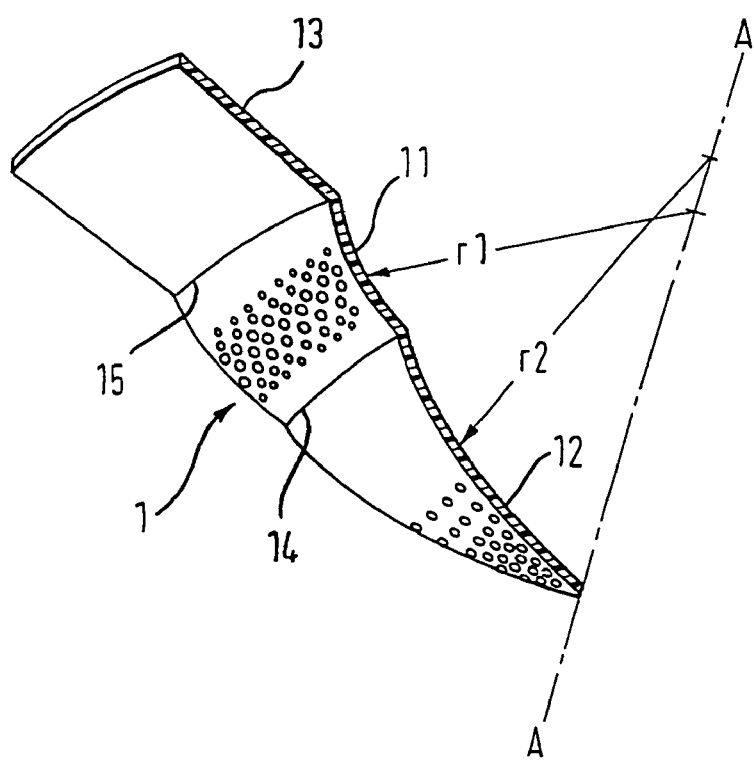
Figure 7:
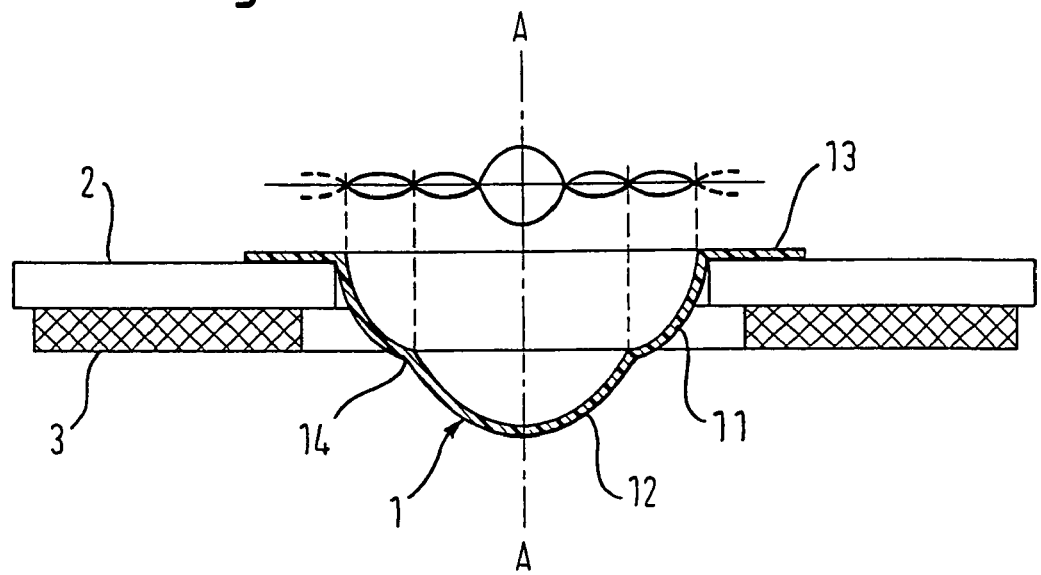
Figure 8:
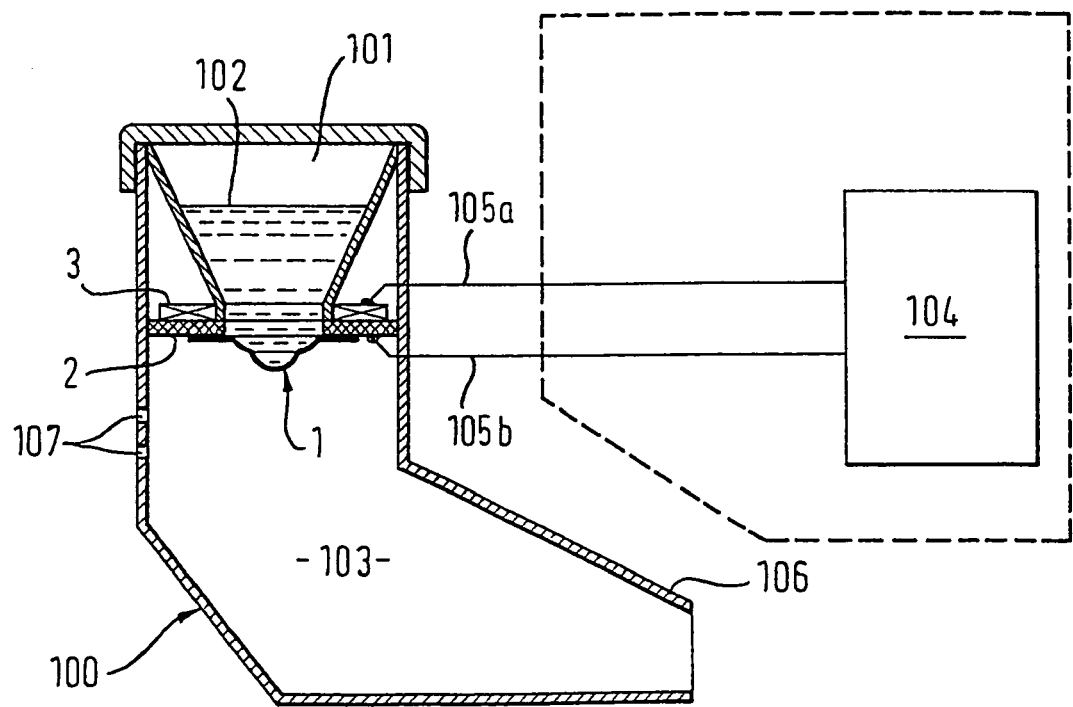
Figure 9:
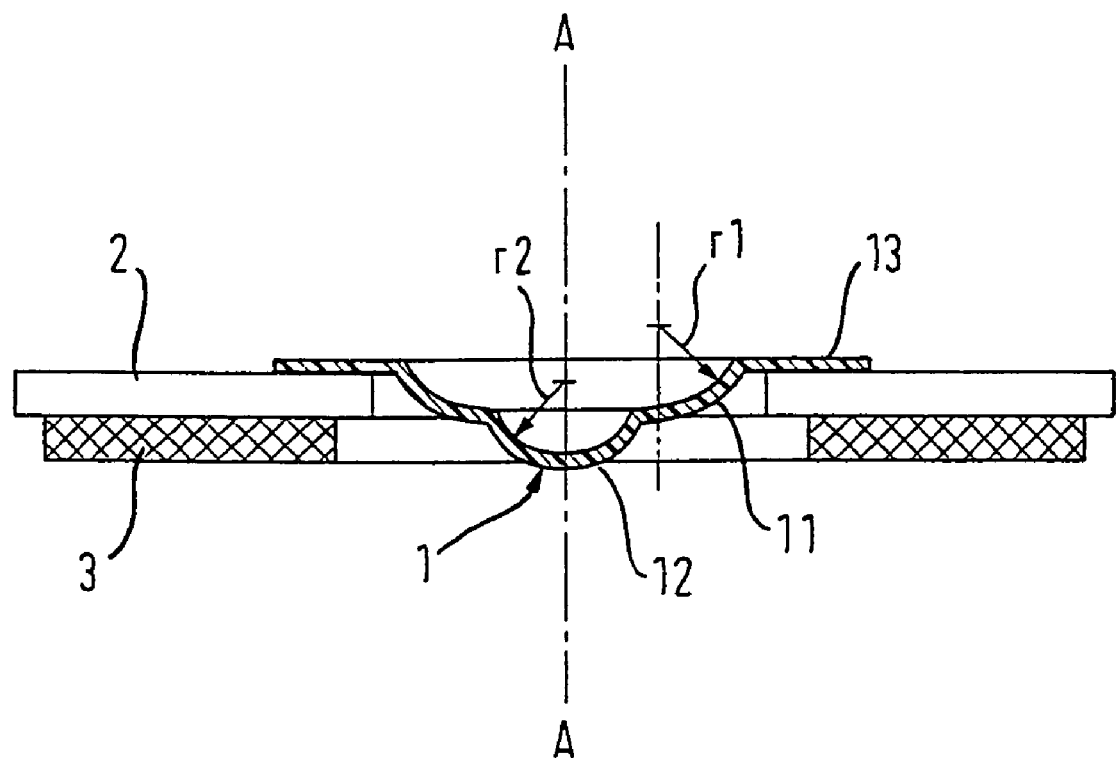

In the following, the invention is described in more detail by means of embodiments with reference to the Figures, wherein the Figures show:

FIG. 1 a first embodiment example of an aerosol generation device according to the invention;

FIG. 2 a second embodiment example of an aerosol generation device according to the invention;

FIG. 3 a third embodiment example of an aerosol generation device according to the invention;

FIG. 4 a fourth embodiment example of an aerosol generation device according to the invention;

FIG. 5 a sectorial cut of a first embodiment example of a membrane according to the invention;

FIG. 6 a sectorial cut of a second embodiment example of a membrane according to the invention;

FIG. 7 a fifth embodiment example of an aerosol generation device according to the invention;

FIG. 8 an embodiment example of an inhalation therapy device according to the invention and FIG. 9 a further embodiment example according to the invention.

FIG. 1 shows a cross-section of an embodiment example of an aerosol generation device according to the invention comprising a membrane 1 and an oscillation generating device 2, 3, which are rotational-symmetrical to the axis of symmetry A-A.

The oscillation generating device 2, 3 comprises a support unit 2 and an electromechanical conversion unit 3, preferably a piezo-electrical conversion unit. The support unit 2 and the electromechanical conversion unit 3 of the embodiment example shown are flat annuli having concentrically aligned openings. The two units 2 and 3 are fixedly connected to each other. The dimensions of both units 2 and 3 of the oscillation generating device are preferably adapted to each other such that the oscillation generating device is caused to generate bending oscillations when excited by an electric drive signal.

The membrane 1 is concentrically arranged towards the openings of the support unit 2 and the electromechanical conversion unit 3 and fixedly connected to the oscillation generating device 2, 3 and, therefore, the oscillation generating device causes the membrane 1 to oscillate when the oscillation generating device 2, 3 itself is excited to oscillate by an electric drive signal. The excitation of the oscillation generating device 2, 3 is preferably performed such that the membrane 1 is caused to oscillate in a desired oscillation state, preferably also bending oscillations, at a desired frequency.

A liquid is typically present on the upper side of the aerosol generation device shown in FIG. 1, i.e. on the concave side of the membrane 1 which is nebulized through the membrane 1. For this purpose, the membrane 1 has small holes preferably tapering beginning with the side facing the liquid.

As may be taken from FIG. 1, the membrane 1 has a first region 11 which is not plane and which is designed in the embodiment example as a spherical segment surface (spherical zone) of a sphere having the radius r1. The first region 11 surrounds a second region 12 which is designed in the embodiment example shown as the calotte of a sphere having the radius r2, wherein, according to the invention, the radii r1 and r2 and, therewith, the curvatures of the two regions 11 and 12 are different.

In connection therewith, the curvature of the regions is to be understood as a curvature of space. For exemplification only, the curvatures of space are designated by the radii of a curvature of a line in order to show the principle of the invention by means of the drawings.

In the embodiment example shown in FIG. 1, r1 is greater than r2. This means that the first region 11 and the second region 12 have different curvatures 1/r1 or 1/r2, wherein the first region 11 in the embodiment shown has a smaller curvature than the second region 12.

However, according to the invention, the membrane can be also designed such that the second region 12 has a smaller curvature than the first region 11. The radius r2 must be therefor selected to be greater than the radius r1 shown in FIG. 2 which Figure is otherwise identical with FIG. 1.

FIG. 3 shows the borderline case in which the radius r2 of the second region 12 is infinite, which means that the second region 12 is plane. Accordingly, in this embodiment example the curvature of the second region 12 is Zero. As for the rest, the embodiment example according to FIG. 3 corresponds to the embodiment examples of FIGS. 1 and 2.

In the embodiment example according to FIG. 4, the radius of the second region 12 is unequal Zero, the second region 12 is, however, curved in one direction which is opposite to the direction of curvature of the first region 11. The amount of the curvature of the second region 12 can be greater or smaller than the amount of the curvature of the first region.

In the embodiment examples shown in FIGS. 1 to 4, a plane region follows the first region 11 as a third region 13 above which the membrane 1 is fastened to the support unit 2 of the oscillation generation device. If the membrane and the support unit are produced as one piece, the plane region 13 can be omitted. Further, it is not necessary that the plane region 13 extents into the opening of the oscillation generation device 2, 3, rather, the first region 11 can extent to the edge of the opening of the oscillation generation device.

A sectorial cut of a membrane 1 is shown by way of example for all membranes 1 according to the invention in FIG. 5 having a first region and a second region 11, 12, in order to thereby principally explain the distribution system of the holes in the membrane. From FIG. 5 the first region 11 having the radius r1, the second region 12 having the radius r2—based on the axis of symmetry A-A each—, and the plane region 13 of the membrane 1 may be taken.

As indicated in FIG. 5, holes are preferably only provided in the first region 11 and in the second region 12 of the membrane 1 while in the third region 13 there are no holes. However, in the embodiment example shown in FIG. 5, the holes are distributed in the first region 11 and in the second region 12 across the entire region.

In the embodiment example shown in FIG. 6, the holes are also only provided in the first region 11 and in the second region 12. In the first region 11, the hole density is however higher about one line which is present in the middle between a first transition edge 14, which is formed at the transition from the first region 11 to the second region 12, and a second transition edge 15, which is formed at the transition from the first region 11 to the third region 13. The hole density decreases towards the transition edges. In the second region 12, the hole densitiy is higher in the middle and decreases towards the first transition edge 14. Instead of a decreasing hole density, it could also be provided that the holes are present at a constant density but only in a band around the center line in the first region 11 or in the middle of the second region 12. These embodiments are advantageously not only in view of the quality of the aerosol to be produced, but also because of a improved durability of the membrane, in that no holes are present weakening the material in the vicinity of the transition edges.

The transition edges 14 and 15 are of particular interest for designing the membrane 1 according to the invention since they allow determination of oscillation node lines for the oscillations resulting in the membrane.

In particular for an embodiment, which is taken as a model here, in which the first region 11 extents to the edge of the opening in the oscillation generation device 2, 3 and which is shown in FIG. 7, the oscillation generation device 2, 3, can be regarded as an active oscillator, which has a certain resonance frequency (operating mode), and the membrane 1 can be regarded as a passive oscillator, the self-contained resonances thereof are excited by the active oscillator (membrane mode). In this model, both oscillators can be viewed independently of each other since a point of intersection is quasi provided between both oscillators by the transition edge 14 between the first region 11 and the second region 12 by means of the determination of an oscillation node line. Above the membrane 1, an oscillation picture is shown in FIG. 7 showing the oscillation nodes and antinodes for a typical excitation of the membrane by the oscillation generation device.

The oscillation picture of FIG. 7 shows that the holes of the membrane 1 must be provided in particular in the middle of the second region 12 since the amplitude of the oscillation is the greatest here and, in addition, the oscillations are simultaneously exactly defined by the transition edge 15. Starting from the center, the hole density may decrease, however, in view of the production process, regular hole arrangements are often advantageous and, therefore, the hole density can be also constant in a zone around the center of the second region 12, but no holes are present outside of the zone (hole density=Zero). This may also be transferred to the first region 11.

The oscillation behaviour of the membrane can be influenced in a targeted manner by providing the transition edges, in particular the transition edge 14, between the first region 11 and the second region 12. Further, the hole density can be increased in the middle of the second region 12, as explained above. Both measures together lead to a preferred design which allows an effective influence on the characteristics of the membrane.

In the aerosol generation device according to the invention, it is in particular achieved that extremely little liquid passes through the membrane without effective nebulization. The amount of liquid adhering to the membrane on the aerosol side is thereby considerably reduced and, therefore, the problem of the adhering liquid droplets and the adverse effect on the nebulization performance connected therewith is eliminated to a great extent. The effect of the design of the membrane according to the invention is so clearly recognizable that it can be dispensed with other measures, e.g. storing the liquid in a reservoir under negative pressure. This aspect is explained in more detail in the inhalation therapy device shown in FIG. 8.

An inhalation therapy device 100 is shown in FIG. 8, wherein a liquid 102 stored in a liquid reservoir 101 is nebulized into a nebulization cavity 103 by means of a membrane 1 according to the invention. The nebulization takes place when the membrane 1 is caused to oscillate, in that the oscillation generation device comprising the support unit 2 and the electromechanical conversion unit 3 a suitable drive signal is submitted. This signal is provided by an electronic drive means 104 and supplied through signal lines 105a and 105b to the electromechanical conversion unit 3. As is shown in FIG. 8, this embodiment provides the advantage that, as a rule, the support unit 2 is made of a conductive material, so that the one signal line 105a can directly be connected to the piezo element 3 and the other signal line 105b can be connected to the support element 2. A patient can breathe-in the aerosol present in the nebulization cavity 103 though the mouth piece 106, wherein environmental air can flow though the air vent openings 107 during the breathing-in phases into the nebulization cavity 103.

When a membrane 1 according to the invention is operated, the liquid reservoir 101 can be designed such that environmental pressure is present in the interior, and that the supply of liquid to the membrane is effected at environmental pressure. Special measures for the generation of a negative pressure in the liquid reservoir 101 are not required. Nevertheless, an undesired accumulation of liquid on the membrane 1 will not take place.

FIG. 9 shows that the invention is not limited to membranes having regions in the form of spherical segment surfaces. Rather, in particular the first region of the membrane surface can also be formed as torus segment surface. A torus is a body which is generated by the rotation of a circular or an elliptical surface about a rotational symmetry axis, wherein the center point of the circle or the of the ellipse are not positioned on this rotational symmetry axis. Hence, it follows in this case that the radius r1 is not based on the rotational symmetry axis of the membrane. The radial components of the curvature (which is the curvature lying in the plane of the drawing and shown in the drawings) can be equal in the different regions 11, 12, however, the tangential component of the curvature of the surface is different (which is the curvature which is perpendicular to the plane of the drawing). The membrane regions may also have other surface forms and are not limited to the forms described above.

The invention claimed is:

1. An aerosol generation device comprising
   an oscillatable membrane for nebulization of a liquid having a first curved nonplanar region and
   an oscillation generating device having a support unit and an electromechanical conversion unit, being fixedly connected to the membrane such that the membrane is excitable into a desired oscillating condition such that a liquid disposed on one side of the membrane is nebulized by passing through holes in the oscillating membrane and is present on the other side of the membrane as an aerosol,
wherein
   the membrane has at least a second region which is surrounded by the first region,
   the first region and the second region have different curvatures, and
   the first region and the second region are both convex outwardly in a single direction when the membrane is at rest.

2. The aerosol generation device according to claim 1, wherein holes are only present in the membrane in the first region and in the second region.

3. An aerosol generation device comprising
   an oscillatable membrane for nebulization of a liquid having a first curved nonplanar region and
   an oscillation generating device having a support unit and an electromechanical conversion unit, being fixedly connected to the membrane such that the membrane is excitable into a desired oscillating condition such that a liquid disposed on one side of the membrane is nebulized by passing through holes in the oscillating membrane and is present on the other side of the membrane as an aerosol,
wherein
   the membrane has at least a second region which is surrounded by the first region and
   the first region and the second region have different curvatures, wherein the holes in the zones distant from the oscillation node lines of the first region have a greater density.

4. An aerosol generation device comprising
   an oscillatable membrane for nebulization of a liquid having a first curved nonplanar region and
   an oscillation generating device having a support unit and an electromechanical conversion unit, being fixedly connected to the membrane such that the membrane is excitable into a desired oscillating condition such that a liquid disposed on one side of the membrane is nebulized by passing through holes in the oscillating membrane and is present on the other side of the membrane as an aerosol,
wherein
   the membrane has at least a second region which is surrounded by the first region and
   the first region and the second region have different curvatures, wherein the holes have a greater density at a center line of the first region.

5. The aerosol generation device according to claim 1, wherein holes are only present in the second region.

6. An aerosol generation device comprising
an oscillatable membrane for nebulization of a liquid having a first curved nonplanar region and
an oscillation generating device having a support unit and an electromechanical conversion unit, being fixedly connected to the membrane such that the membrane is excitable into a desired oscillating condition such that a liquid disposed on one side of the membrane is nebulized by passing through holes in the oscillating membrane and is present on the other side of the membrane as an aerosol,
wherein
the membrane has at least a second region which is surrounded by the first region and
the first region and the second region have different curvatures, wherein the holes in the zones distant from the oscillation node lines of the second region have a greater density.

7. An aerosol generation device comprising
an oscillatable membrane for nebulization of a liquid having a first curved nonplanar region and
an oscillation generating device having a support unit and an electromechanical conversion unit, being fixedly connected to the membrane such that the membrane is excitable into a desired oscillating condition such that a liquid disposed on one side of the membrane is nebulized by passing through holes in the oscillating membrane and is present on the other side of the membrane as an aerosol,
wherein
the membrane has at least a second region which is surrounded by the first region and
the first region and the second region have different curvatures, wherein the holes have a greater density in the middle of the second region.

8. The aerosol generation device according to claim 1, wherein no holes are present in the membrane in the vicinity of transition edges between the regions.

9. The aerosol generation device according to claim 1, wherein the first region is surrounded by a third region the curvature of which is Zero.

10. The aerosol generation device according to claim 1, wherein the first region extends to the edge of an opening of the oscillation generating device.

11. The aerosol generation device according to claim 1, wherein the oscillation generating device comprises a support unit and an electromechanical conversion unit, which are connected to each other.

12. The aerosol generation device according to claim 1, wherein the oscillation generating device excites the membrane to bending oscillations.

13. The aerosol generation device according to claim 1, wherein the membrane and the oscillation generating device are rotational-symmetrically designed.

14. An inhalation therapy device comprising
a liquid storing means for storing a liquid to be nebulized, and
an aerosol generation device according to claim 1, wherein the supply of the liquid is performed from the liquid storing means to the membrane at environmental pressure.

15. The aerosol generation device according to claim 11, wherein the electromechanical conversion unit comprises a piezo-electric conversion unit.

* * * * *